United States Patent
Xu et al.

(10) Patent No.: US 11,993,799 B1
(45) Date of Patent: May 28, 2024

(54) METHOD FOR PREPARING CARBON SOURCE FOR WASTEWATER TREATMENT BY USING KITCHEN WASTE

(71) Applicant: HANGZHOU NANDA ENVIRONMENTAL PROTECTION TECHNOLOGY CO., LTD, Hangzhou (CN)

(72) Inventors: Jianlin Xu, Hangzhou (CN); Bin Gu, Hangzhou (CN); Yuan Fu, Hangzhou (CN); Zhenggeng Qiu, Hangzhou (CN)

(73) Assignee: HANGZHOU NANDA ENVIRONMENTAL PROTECTION TECHNOLOGY CO., LTD, Hangzhou (CN)

( * ) Notice: Subject to any disclaimer, the term of this patent is extended or adjusted under 35 U.S.C. 154(b) by 0 days.

(21) Appl. No.: 18/499,231

(22) Filed: Nov. 1, 2023

Related U.S. Application Data

(63) Continuation of application No. PCT/CN2023/101671, filed on Jun. 21, 2023.

(30) Foreign Application Priority Data

Dec. 28, 2022 (CN) .......................... 202211690524.9

(51) Int. Cl.
*C12P 1/04* (2006.01)
*C02F 3/12* (2023.01)

(52) U.S. Cl.
CPC .............. *C12P 1/04* (2013.01); *C02F 3/1263* (2013.01); *C02F 2305/06* (2013.01)

(58) Field of Classification Search
CPC .................................. C12P 1/04; Y02W 10/10
See application file for complete search history.

(56) References Cited

U.S. PATENT DOCUMENTS

| | | | |
|---|---|---|---|
| 10,214,436 B2 | 2/2019 | Ogawa et al. | |
| 10,611,657 B2 | 4/2020 | Dai et al. | |
| 11,414,332 B2 | 8/2022 | Fujioka | |

FOREIGN PATENT DOCUMENTS

| | | |
|---|---|---|
| CN | 112174337 A | 1/2021 |
| CN | 114835250 A | 8/2022 |
| CN | 115846374 A | 3/2023 |
| KR | 20140000576 A | 1/2014 |

*Primary Examiner* — Tekchand Saidha
(74) *Attorney, Agent, or Firm* — True Shepherd LLC; Andrew C. Cheng

(57) ABSTRACT

A method for preparing a carbon source for wastewater treatment by using kitchen waste, comprises: adding a complex microbial inoculant into the kitchen waste; and phase-change degrading the kitchen waste into a phase-change liquid under aerobic fermentation of the complex microbial inoculant; wherein the phase-change liquid is the carbon source for wastewater treatment; the complex microbial inoculant comprises: a microbial agent comprising aerobic bacteria; and an excipient comprising an Fe-based MOF (metal-organic framework) nanocomposite. According to the method, the kitchen waste is treated under aerobic fermentation to prepare the carbon source, a carbon-nitrogen ratio is greater than 40, and the carbon source is used to supplement a carbon source in a sewage treatment process of a sewage plant, which significantly improves nitrogen and phosphorus removal effects of sewage treatment in the sewage plant, and provides theoretical foundation and basis for resource utilization of the kitchen waste.

8 Claims, 1 Drawing Sheet

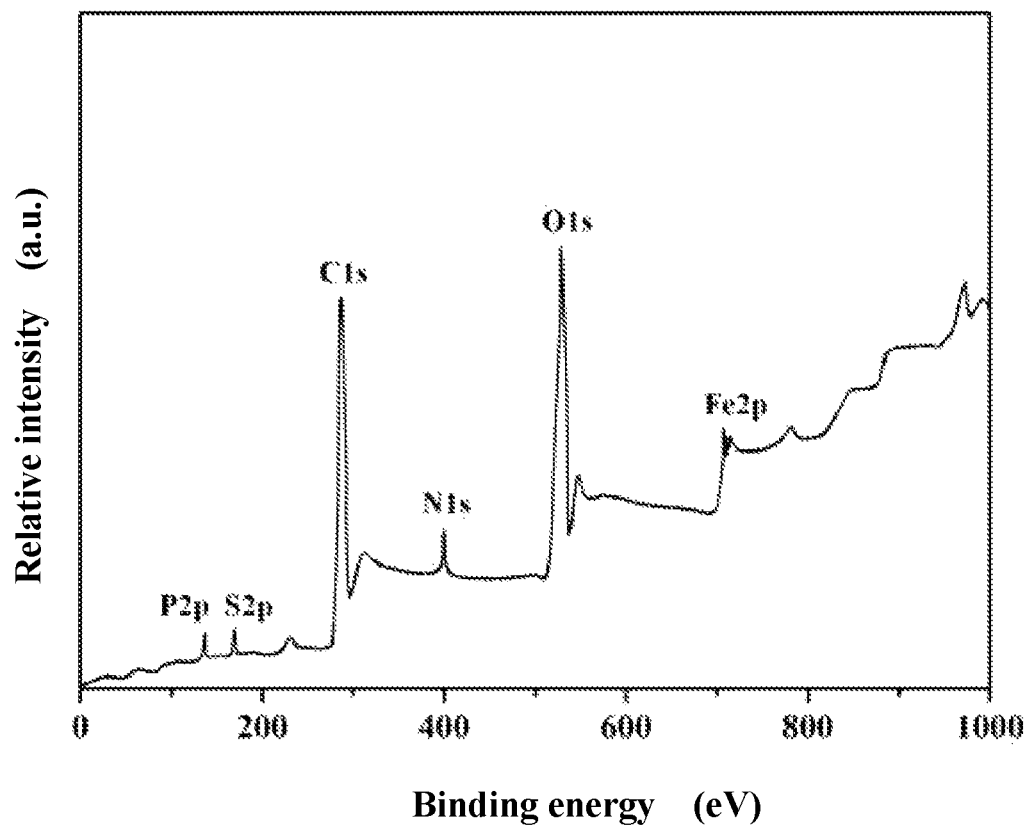

METHOD FOR PREPARING CARBON SOURCE FOR WASTEWATER TREATMENT BY USING KITCHEN WASTE

CROSS-REFERENCE TO RELATED APPLICATIONS

This application is a continuation of International Patent Application No. PCT/CN2023/101671 with a filing date of Jun. 21, 2023, designating the United States, now pending, and further claims priority to Chinese Patent Application No. 202211690524.9 with a filing date of Dec. 28, 2022. The content of the aforementioned applications, including any intervening amendments thereto, are incorporated herein by reference.

TECHNICAL FIELD

The present invention relates to the technical field of garbage disposal, in particular to a method for preparing a carbon source for wastewater treatment by using kitchen waste.

BACKGROUND

The kitchen waste refers to the garbage produced in residents' daily life and food processing, catering services, enterprise feeding, etc., including discarded vegetable leaves, leftovers, fruit peels, eggshells, soup rice, bones, etc., and its main resources are household kitchens, restaurants, canteens, markets and other food processing-related industries. The kitchen waste contains extremely high moisture and organic matter, which is easily perishable and causes foul smell.

The survey research finds that the kitchen waste has a high organic matter content and is easily degraded by microorganisms. Main components of its organic matter are starch, protein, fat and cellulose, and high-quality carbohydrates such as amino acids, sugars and fatty acids are generated after aerobic microbial hydrolysis and acidification. The starch is a high molecular glucose polymer, including two forms such as amylose and amylopectin, which can be hydrolyzed to glucose by hydrolase. The protein can be degraded into polypeptides and amino acids through the action of a protein degradation enzyme, the fat can be degraded into glycerol and fatty acids by lipase, the degradation of the cellulose is mainly achieved through the synergistic effect of multiple enzymes, and finally the cellulose is converted into usable glucose. At the same time, the sugars, the amino acids, etc. have better water solubility, which are easily migrated to a liquid phase system to form organic wastewater with high COD (chemical oxygen demand-Dichromate method). Such low-molecular-weight organic matters are finally converted into $H_2O$ and $CO_2$ through biological metabolism processes such as glucolysis, tricarboxylic acid cycle and oxidative phosphorylation, and provide energy for life activities. Therefore, a phase-change liquid rich in the sugars, the amino acids and low-molecular-weight fatty acids has good biodegradability, which can be used as a high-quality carbon source for microorganisms in sewage treatment, to achieve "turning waste into wealth".

In recent years, since the domestic waste classification system is vigorously promoted in China, the kitchen waste treatment capacity is increased, the treatment plants are increased year by year, anaerobic digestion is mainly applied to large-scale kitchen waste treatment plants, and aerobic fermentation is only applied to small and medium-sized kitchen waste treatment plants currently.

SUMMARY

An object of the present invention is to provide a method for preparing a carbon source for wastewater treatment by using kitchen waste. According to the method, the kitchen waste is treated under aerobic fermentation to prepare the carbon source, a carbon-nitrogen ratio is greater than 40, and the carbon source is used to supplement a carbon source in a sewage treatment process of a sewage plant, which significantly improves nitrogen and phosphorus removal effects of sewage treatment in the sewage plant, and provides theoretical foundation and basis for resource utilization of the kitchen waste The present invention uses the following technical solution to achieve the above object:

a method for preparing a carbon source for wastewater treatment by using kitchen waste, comprising: adding a complex microbial inoculant into the kitchen waste; and phase-change degrading the kitchen waste into a phase-change liquid under aerobic fermentation of the complex microbial inoculant; wherein the phase-change liquid is the carbon source for wastewater treatment;

the complex microbial inoculant comprises: a microbial agent comprising aerobic bacteria; and an excipient comprising an Fe-based MOF (metal-organic framework) nanocomposite. According to the present invention, the organic matter of the kitchen waste is degraded into low-molecular-weight organic matter, $H_2O$, $CO_2$, $NH_4^+$—N, $SO_4^{2-}$ and other inorganic salts by the complex microbial inoculant through dissimilation under aerobic conditions, and main characteristics of the prepared carbon source for wastewater treatment are complex water-quality components, high content of organic matter and inorganic salts containing ammonia nitrogen, etc. The degradation process basically does not include a path for producing marsh gas, and the nitrogen consumption in ammoxidation and denitrification is more thorough, so that the carbon source has a higher carbon content, the carbon-nitrogen ratio is greater than 40:1, and the carbon source has better biodegradability. There are many species of compound low-molecular-weight dissolved organic matters produced during an oxidation process of the kitchen waste, which are especially suitable for supplementing the carbon source for wastewater with a low carbon-nitrogen ratio, such as domestic sewage, landfill leachate and industrial wastewater, to improve the treatment efficiency of such wastewater. At the same time, the Fe-based MOF nanocomposite used as the excipient is compounded with the microbial agent to prepare the complex microbial inoculant, which can effectively enhance the degradation of the complex inoculant on the kitchen waste, accelerate the biological degradation process and effectively increase the degradation rate of organic matter in the kitchen waste. Moreover, the contents of the components of the prepared carbon source have been adjusted and improved to a certain extent, which can effectively enhance the effect of wastewater treatment and improve the nitrogen and phosphorus removal effects of sewage treatment as a supplementary carbon source in the wastewater treatment process. In addition, the growth of microorganisms in activated sludge can be promoted effectively, and the activity of sludge is enhanced, so that the activated sludge maintains excellent agglomeration and sedimentation. The reason may lie in that the present invention uses modification of N-(n-butyl) thiophosphoric triamide to prepare the Fe-based MOF nanocomposite, which is applied to the complex microbial inoculant as the excipient, thereby effectively improving the degradation rate of organic matter by microbial degradation. It is guessed that the nanocomposite has stronger adsorption capacity, and its internal structure is adjusted to a certain extent during the preparation process, so as to reduce ammonia toxicity by adsorbing ammonia nitrogen, improve the living environment of microorganisms and improve its biological activity; at the same time, the nanocomposite can also promote the interaction between microorganisms and improve the enzyme activity, thereby effectively converting complicated organic matter into low-molecular-weight organic matter and promoting its biological degradation, so as to improve the biological degradation rate of the kitchen waste.

Specifically, the method for preparing the carbon source for wastewater treatment by using the kitchen waste comprises the following steps:

sorting and removing sundries from the kitchen waste, adding water according to a solid-liquid ratio of 1 g: (1-1.2) mL to obtain a mixture, placing the mixture in a pulverizer for crushing and pulping, filtering with a filter screen, heating the filtered kitchen waste slurry for 30-60 min at 75-90° C., and extracting and removing 70%-80% of waste grease with a three-phase separator; adding the complex microbial inoculant into the kitchen waste slurry, adjusting an initial pH value to 6.5-7.2, performing open fermentation at 35-45° C. for 4-6 d; and centrifuging the fermented material for 10-15 min at 4000-4200 rpm for solid-liquid separation, and taking a supernatant; wherein the supernatant is the carbon source for wastewater treatment.

In a specific embodiment, a mass ratio of the microbial agent to the excipient is 1:(3-10).

In a specific embodiment, the microbial agent comprises 10-16 parts of *Bacillus licheniformis*, 15-20 parts of *Bacillus subtilis*, 8-14 parts of yeast and 10-15 parts of *Pediococcus acidilactici* in parts by weight.

The present invention further discloses a preparation method of the above complex microbial inoculant, specifically comprising the following steps:

placing *Bacillus licheniformis*, *Bacillus subtilis* and yeast on an LB solid medium, respectively, placing *Pediococcus acidilactici* on an MRS solid medium, culturing for 24 h at 30-42° C., then inoculating into a fermentation liquid shake flask separately, and performing shaking culture for 24-32 h at 130-150 r/min and 30-42° C. to obtain a seed liquid of each strain;

then inoculating the seed liquid of each strain into a culture material in a fermentation tank according to a volume ratio of 1:(380-420) for fermentation, respectively, with a temperature of 30-42° C., a stirring speed of 130-150 r/min, pH of 6-7, dissolved oxygen of 25%-35% and a tank pressure of 0.03-0.05 MPa; then centrifuging for 10-15 min at 6000-6400 r/min, and diluting precipitates with sterile water to obtain a microbial inoculum of each strain with a concentration of viable bacteria of $10^9$-$10^{10}$ CFU/mL; and mixing the microbial inoculum of each strain according to some parts by weight to obtain the microbial agent, then compounding with a vector, and drying below 45° C. to contain 10%-14% of moisture, to obtain the complex microbial inoculant.

In a specific embodiment, an addition amount of the complex microbial inoculant accounts for 8-12 wt % of the kitchen waste slurry.

In a specific embodiment, the Fe-based MOF nanocomposite is prepared by the following steps: mixing an Fe-based metal-organic framework and graphene oxide, performing one-step solvothermal synthesis to obtain Fe-MOF@GO, and then mixing the Fe-MOF@GO with N-(n-butyl) thiophosphoric triamide and performing high-temperature treatment to obtain the Fe-based MOF nanocomposite.

Further, a preparation method of the above Fe-based MOF nanocomposite specifically comprises the following steps:

Fe-MOF@GO is prepared by a conventional preparation method in the prior art;

Fe-MOF@GO and N-(n-butyl) thiophosphoric triamide are placed into two open combustion boats, respectively; the combustion boat containing N-(n-butyl) thiophosphoric triamide is placed at an upper air outlet of a quartz tube, and the other combustion boat is placed at a lower air outlet thereof, with a spacing of 2.8-3.2 cm; then, vacuumizing is performed, argon gas is introduced with an air flow of 95-105 mL/min, and a temperature is raised to 680-720° C. at a heating rate of 2-3° C./min and maintained for 1.5-3.5 h; and cooling is performed to obtain the Fe-based MOF nanocomposite.

In a specific embodiment, a mass ratio of Fe-MOF@GO to N-(n-butyl) thiophosphoric triamide is 1:(4-6).

In a specific embodiment, a carbon-nitrogen ratio of the carbon source for wastewater treatment is greater than 40:1.

In a specific embodiment, in the carbon source for wastewater treatment, a COD content is 20000-40000 mg/L, a $NH_4^+$—N content is 200-600 mg/L, a TN (total nitrogen) content is 300-500 mg/L, and a TP (total phosphorus) content is 30-50 mg/L.

More preferably, in the method for preparing the carbon source for wastewater treatment by using the kitchen waste, a mixed solution of a novel ionic liquid and water is used to replace water. The present invention uses modification of sodium N-methyltaurate to prepare the novel ionic liquid, which is compounded with water to pretreat the kitchen waste, and then the complex microbial inoculant is used for degradation, to effectively promote the degradation process of the kitchen waste and further increase the degradation rate of organic matter. Physicochemical properties of the prepared carbon source are improved, the C/N ratio is further increased, and the carbon source is applied to the sewage treatment process, which further enhances the nitrogen and phosphorus removal effects of sewage treatment, promotes the growth of microorganisms in activated sludge and improves the activity of sludge, so that the activated sludge maintains excellent agglomeration and sedimentation. The reason may lie in that the novel ionic liquid prepared by the present invention has better solubility for biological macromolecules such as cellulose, which provides more convenient conditions for the degradation process of the complex microbial inoculant, better promotes the occurrence of degradation, improves the degradation efficiency and then has beneficial effects on the prepared carbon source.

In a specific embodiment, a mass ratio of the novel ionic liquid to water is 1:(2-3).

It shall be noted that a preparation method of the novel ionic liquid comprises the following steps:

adding imidazole and NaH to THF, stirring for 40-60 min at 0° C., raising a temperature to room temperature, adding 1-bromohexane, continuing to stir for 20-24 h, then washing a product with water and extracting with THF, and purifying with a silica gel column to obtain 1-n-hexylimidazole;

adding 1,6-dibromohexane to acetonitrile, performing heating reflux, then adding a solution of 1-n-hexylimidazole in acetonitrile dropwise, reacting for 24-26 h at 85-95° C., removing a solvent by reduced pressure distillation, and washing with anhydrous ether to obtain an intermediate product S; and mixing the intermediate product S, sodium N-methyltaurate and potassium carbonate, adding acetonitrile, and reacting for 68-76 h at 85-95° C.; filtering to remove solids, performing reduced pressure distillation, washing with anhydrous ether, then dissolving in ultrapure water, adding excess $LiNTf_2$ for anion exchange, adding dichloromethane for extraction and anhydrous sodium sulfate for drying after 5-8 h, then repeating the operation for 1-2 times, and drying a solvent by distillation to obtain the novel ionic liquid.

In a specific embodiment, a molar ratio of imidazole to NaH is 1:(1-1.1); a solid-to-liquid ratio of imidazole to THF is (0.3-0.4) g: 1 mL; and a molar ratio of 1-bromohexane to imidazole is 1:(0.9-1.1).

In a specific embodiment, a solid-to-liquid ratio of 1,6-dibromohexane to acetonitrile is (0.8-1.2) g: 1 mL; a concentration of the solution of 1-n-hexylimidazole in acetonitrile is 0.1-0.2 g/mL; and a molar ratio of 1-n-hexylimidazole to 1,6-dibromohexane is 1:(13-15).

In a specific embodiment, a molar ratio of the intermediate product S, sodium N-methyltaurate and potassium carbonate is 1:(1.2-1.3):(6-7); and a solid-to-liquid ratio of the intermediate product S to acetonitrile is (0.010-0.025) g: 1 mL.

The present invention also discloses a use of the carbon source prepared by the method for preparing the carbon source for wastewater treatment by using the kitchen waste in improving sewage treatment efficiency in a sewage plant.

In a specific embodiment, a usage amount of the carbon source accounts for 0.25-3 wt % of sewage in a sewage treatment process.

Another object of the present invention is to provide an application of the Fe-based MOF nanocomposite in preparing the complex microbial inoculant for degradation of the kitchen waste.

Another object of the present invention is to provide an application of the Fe-based MOF nanocomposite in preparing the carbon source for wastewater treatment.

Compared with the prior art, the present invention has the following beneficial effects:

According to the present invention, the organic matter of the kitchen waste is degraded into low-molecular-weight organic matter, $H_2O$, $CO_2$, $NH_4^+$—N, $SO_4^{2-}$ and other inorganic salts by the complex microbial inoculant through dissimilation under aerobic conditions, and the prepared carbon source for wastewater treatment has the carbon-nitrogen ratio of greater than 40:1 and better biodegradability. In the complex microbial inoculant, the Fe-based MOF nanocomposite is used as the excipient, which is compounded with the microbial agent, thereby effectively enhancing the degradation of the complex inoculant on the kitchen waste, accelerating the biological degradation process and effectively increasing the degradation rate of organic matter in the kitchen waste. Moreover, the carbon-nitrogen ratio of the prepared carbon source is further increased, which can effectively enhance the effect of wastewater treatment and improve the nitrogen and phosphorus removal effects of sewage treatment as a supplementary carbon source in the wastewater treatment process. In addition, the growth of microorganisms in activated sludge can be promoted effectively, and the activity of sludge is enhanced. Besides, the present invention uses modification of sodium N-methyltaurate to prepare the novel ionic liquid, which is compounded with water to pretreat the kitchen waste, to effectively promote the degradation process of the kitchen waste and further increase the degradation rate of organic matter. Physicochemical properties of the prepared carbon source are improved, the C/N ratio is further increased, and the carbon source is applied to the sewage treatment process, which further enhances the nitrogen and phosphorus removal effects of sewage treatment, promotes the growth of microorganisms in activated sludge and improves the activity of sludge, so that the activated sludge maintains excellent agglomeration and sedimentation.

Therefore, the present invention provides the method for preparing the carbon source for wastewater treatment by using the kitchen waste. According to the method, the kitchen waste is treated under aerobic fermentation to prepare the carbon source, the carbon-nitrogen ratio is greater than 40:1, and the carbon source is used to supplement a carbon source in a sewage treatment process of a sewage plant, which significantly improves nitrogen and phosphorus removal effects of sewage treatment in the sewage plant, and provides theoretical foundation and basis for resource utilization of the kitchen waste.

BRIEF DESCRIPTION OF DRAWINGS

FIG. 1 is an XPS test result of an Fe-based MOF nanocomposite prepared in Embodiment 1 of the present invention.

DESCRIPTION OF EMBODIMENTS

In order to make the objects, technical solutions and advantages of embodiments of the present invention clearer, implementation manners of the present invention will be elaborated below in detail in conjunction with the embodiments. However, those of ordinary skill in the art can understand that in the embodiments of the present invention, in order for readers to better understand the present application, many technical details are presented. However, even without these technical details and various changes and modifications based on the following embodiments, the technical solutions claimed by the present application may also be achieved.

In the embodiments of the present invention, the preservation number of *Bacillus licheniformis* is CGMCC 1.7461; the preservation number of *Bacillus subtilis* is ATCC 11774; the yeasts are BY4741 bacteria, purchased from Beijing Xinghua Yueyang Biotechnology Co., Ltd.; and *Pediococcus acidilactici* is purchased from Shanghai Jiachu Bioengineering Co., Ltd., and its strain number is SHBCC D12389.

The preparation method of Fe-MOF@GO used in the embodiments of the present invention is the prior art, specifically comprising the following steps:

adding GO and $FeCl_3 \cdot 6H_2O$ (a mass ratio of the two is 0.0445:1) to N,N-dimethylformamide, respectively, and performing ultrasonic mixing uniformly to obtain a GO solution (a concentration of 2 mg/mL) and a solution A (a concentration of 0.045 g/mL); adding 2-aminoterephthalic acid to DMF (a solid-liquid ratio of 0.015 g: 1 mL), wherein a mass ratio of 2-aminoterephthalic acid to $FeCl_3 \cdot 6H_2O$ is 0.34:1, stirring to form a homogeneous solution, adding the GO solution immediately, adding the solution A after 0.5 h, stirring for 0.5 h, and performing heat preservation for 24 h at 110° C.; after complete cooling, performing suction filtration, washing and freeze-drying for 24 h to obtain Fe-MOF@GO.

The basic composition of the kitchen waste is shown in Table 1:

TABLE 1

Basic composition of the kitchen waste

| Raw material | Moisture content (%) | TOC (mg/g) | TKN (mg/g) | Grease (%) | Salinity (%) | pH |
|---|---|---|---|---|---|---|
| Kitchen waste | 74.5 | 503.4 | 28.3 | 8.13 | 0.73 | 4.8-5.2 |

Embodiment 1

A method for preparing a carbon source for wastewater treatment by using kitchen waste:

Sundries such as metals and plastics from the kitchen waste were sorted and removed, water was added according to a solid-liquid ratio of 1 g: 1 mL to obtain a mixture, the mixture was placed in a pulverizer for crushing and pulping and filtered with a filter screen (φ1 mm), about 40% of protein in the kitchen waste was intercepted in the filter residue, the filtered kitchen waste slurry was heated for 35 min at 80° C., and 75% of waste grease was extracted and removed with a three-phase separator; a complex microbial inoculant was added into the kitchen waste slurry, wherein an addition amount of the complex microbial inoculant accounted for 10 wt % of the kitchen waste slurry, an initial pH value was adjusted to 6.8, open fermentation was performed at 40° C. for 5 d; and the fermented material was centrifuged for 15 min at 4000 rpm for solid-liquid separation, and a supernatant was taken; wherein the supernatant was the carbon source for wastewater treatment.

The complex microbial inoculant comprised a microbial agent and an excipient, wherein a mass ratio of the two was 1:6; and the microbial agent comprised 13 parts of *Bacillus licheniformis*, 18 parts of *Bacillus subtilis*, 12 parts of yeast and 13 parts of *Pediococcus acidilactici* in parts by weight.

Preparation of the complex microbial inoculant:

*Bacillus licheniformis*, *Bacillus subtilis* and yeast were placed on an LB solid medium, respectively, *Pediococcus acidilactici* was placed on an MRS solid medium, cultured for 24 h at 30-42° C., and then inoculated into a fermentation liquid shake flask separately, and shaking culture was performed for 24 h at 130-150 r/min and 30-42° C. to obtain a seed liquid of each strain;

then the seed liquid of each strain was inoculated into a culture material in a fermentation tank according to a volume ratio of 1:400 for fermentation, respectively, with a temperature of 30-42° C., a stirring speed of 135 r/min, pH of 6-7, dissolved oxygen of 30% and a tank pressure of 0.04 MPa; then the mixture was centrifuged for 10 min at 6000 r/min, and precipitates were diluted with sterile water to obtain a microbial inoculum of each strain with a concentration of viable bacteria of $10^{10}$ CFU/mL; and the microbial inoculum of each strain was mixed according to some parts by weight to obtain the microbial agent, then compounded with a vector, and dried below 45° C. to contain 12% of moisture, to obtain the complex microbial inoculant.

Formula of the LB solid medium: 10 g of tryptone, 5 g of yeast powder, 10 g of NaCl and 18.5 g of agar powder, filling to 1 L, and adjusting pH to 7.2 with NaOH.

Formula of the MRS solid medium: 10 g of tryptone, 10 g of beef extract, 10 g of NaCl, 5 g of yeast powder, 2 g of diammonium citrate, 20 g of glucose, 1 mL of Tween 80, 5 g of sodium acetate, 2 g of $K_2HPO_4$, 0.58 g of $MgSO_4 \cdot 7H_2O$, 0.25 g of manganese sulfate and 18 g of agar, filling to 1 L, and adjusting pH to 6.5.

Formula of a liquid fermentation medium: 10 g of corn flour, 5 g of soybean meal, 5 g of glucose, 2 g of peptone, 1 g of NaCl, 1 g of $K_2HPO_4$ and 0.2 g of $MgSO_4 \cdot 7H_2O$, filling to 1 L.

The above excipient was an Fe-based MOF nanocomposite, and its preparation method was as follows:

Fe-MOF@GO and N-(n-butyl) thiophosphoric triamide were placed into two open combustion boats at a mass ratio of 1:5.1, respectively; the combustion boat containing N-(n-butyl) thiophosphoric triamide was placed at an upper air outlet of a quartz tube, and the other combustion boat was placed at a lower air outlet thereof, with a spacing of 3 cm; then, vacuumizing was performed, argon gas was introduced with an air flow of 100 mL/min, and a temperature was raised to 700° C. at a heating rate of 2° C./min and maintained for 3 h; and the nanocomposite was taken out and obtained after cooling.

Embodiment 2

A method for preparing a carbon source for wastewater treatment by using kitchen waste was different from Embodiment 1 in that the complex microbial inoculant was prepared by the present embodiment and an addition amount of the complex microbial inoculant accounted for 8.4 wt % of the kitchen waste slurry.

The complex microbial inoculant comprised a microbial agent and an excipient, wherein a mass ratio of the two was 1:8; and the microbial agent comprised 11 parts of *Bacillus licheniformis*, 15 parts of *Bacillus subtilis*, 8 parts of yeast and 15 parts of *Pediococcus acidilactici* in parts by weight.

A preparation method of the above complex microbial inoculant was the same as Embodiment 1.

The above excipient was an Fe-based MOF nanocomposite, and its preparation method was different from Embodiment 1 in that:

a mass ratio of Fe-MOF@GO to N-(n-butyl) thiophosphoric triamide was 1:4.2.

Embodiment 3

A method for preparing a carbon source for wastewater treatment by using kitchen waste was different from Embodiment 1 in that the complex microbial inoculant was prepared by the present embodiment and an addition amount of the complex microbial inoculant accounted for 12 wt % of the kitchen waste slurry.

The complex microbial inoculant comprised a microbial agent and an excipient, wherein a mass ratio of the two was 1:10; and the microbial agent comprised 15 parts of *Bacillus licheniformis*, 20 parts of *Bacillus subtilis*, 14 parts of yeast and 14 parts of *Pediococcus acidilactici* in parts by weight.

A preparation method of the above complex microbial inoculant was the same as Embodiment 1.

The above excipient was an Fe-based MOF nanocomposite, and its preparation method was different from Embodiment 1 in that:

a mass ratio of Fe-MOF@GO to N-(n-butyl) thiophosphoric triamide was 1:5.8.

Embodiment 4

A method for preparing a carbon source for wastewater treatment by using kitchen waste was different from Embodiment 1 in that the complex microbial inoculant was prepared by the present embodiment and an addition amount of the complex microbial inoculant accounted for 9 wt % of the kitchen waste slurry.

The complex microbial inoculant comprised a microbial agent and an excipient, wherein a mass ratio of the two was 1:3; and the microbial agent comprised 10 parts of *Bacillus licheniformis*, 15 parts of *Bacillus subtilis*, 8 parts of yeast and 10 parts of *Pediococcus acidilactici* in parts by weight.

A preparation method of the above complex microbial inoculant was the same as Embodiment 1.

The above excipient was an Fe-based MOF nanocomposite, and its preparation method was different from Embodiment 1 in that:

a mass ratio of Fe-MOF@GO to N-(n-butyl) thiophosphoric triamide was 1:4.

Embodiment 5

A method for preparing a carbon source for wastewater treatment by using kitchen waste:

Sundries such as metals and plastics from the kitchen waste were sorted and removed, a mixed solution of a novel ionic liquid/water (a mass ratio of 1:2.5) was added according to a solid-liquid ratio of 1 g: 1 mL to obtain a mixture, the mixture was placed in a pulverizer for crushing and pulping and filtered with a filter screen (φ1 mm), about 40% of protein in the kitchen waste was intercepted in the filter residue, the filtered kitchen waste slurry was heated for 35 min at 80° C., and 75% of waste grease was extracted and removed with a three-phase separator; a complex microbial inoculant was added into the kitchen waste slurry, wherein an addition amount of the complex microbial inoculant accounted for 10 wt % of the kitchen waste slurry, an initial pH value was adjusted to 6.8, open fermentation was performed at 40° C. for 5 d; and the fermented material was centrifuged for 15 min at 4000 rpm for solid-liquid separation, and a supernatant was taken; wherein the supernatant was the carbon source for wastewater treatment.

The complex microbial inoculant and its preparation method were the same as Embodiment 1.

A preparation method of an Fe-based MOF nanocomposite was the same as Embodiment 1.

Preparation of the above novel ionic liquid:

Imidazole and NaH (a molar ratio of the two was 1:1.05) were added to THF, wherein a solid-to-liquid ratio of imidazole to THF was 0.35 g: 1 mL, and the mixture was stirred for 50 min at 0° C., a temperature was raised to room temperature, 1-bromohexane (a molar ratio with imidazole was 1:1) was added and stirred continuously for 24 h, then a product was washed with water and extracted with THF, and purified with a silica gel column to obtain 1-n-hexylimidazole, $^1$H NMR (400 MHz, CDCl$_3$) δ 7.59, 7.19, 6.84 (3H, IMI-H), 3.92 (t, 2H, —CH$_2$), 1.92 (m, 2H, —CH$_2$), 1.23-1.34 (6H, —CH$_2$), 0.88 (s, 3H, —CH$_3$);

1,6-dibromohexane was added to acetonitrile according to a solid-to-liquid ratio of 1 g: 1 mL, heating reflux was performed, then a solution of 1-n-hexylimidazole (a molar ratio with 1,6-dibromohexane was 1:14) in acetonitrile with a concentration of 0.14 g/mL was added dropwise and subjected to a reaction for 24 h at 90° C., a solvent was removed by reduced pressure distillation, and the mixture was washed with anhydrous ether (3×5 mL) to obtain an intermediate product S; $^1$H NMR (400 MHz, CDCl$_3$) δ 10.13, 7.73, 7.48 (3H, IMI-H), 4.45 (t, 2H, —CH$_2$), 4.29 (t, 2H, —CH$_2$), 3.58 (t, 2H, —CH$_2$), 1.82-2.04 (m, 6H, —CH$_2$), 1.29-1.37 (10H, —CH$_2$), 0.88 (s, 3H, —CH$_3$); and the intermediate product S, sodium N-methyltaurate and potassium carbonate (a molar ratio of the three was 1:1.26:6.4) were mixed, acetonitrile (a solid-to-liquid ratio of the intermediate product S to acetonitrile was 0.018 g: 1 mL) was added, and subjected to a reaction for 72 h at 90° C.; solids were removed by filtering, reduced pressure distillation was performed, the mixture was washed with anhydrous ether (3×5 mL) and then dissolved in ultrapure water, excess LiNTf$_2$ was added for anion exchange, dichloromethane was added for extraction and anhydrous sodium sulfate was added for drying after 6 h, then the operation was repeated for 2 times, and a solvent was dried by distillation to obtain the novel ionic liquid; $^1$H NMR (400 MHz, CDCl$_3$) δ 10.43, 8.01, 7.69 (3H, IMI-H), 4.49 (t, 2H, —CH$_2$), 4.21 (t, 2H, —CH$_2$), 3.48 (t, 2H, —CH$_2$), 3.01 (t, 2H, —CH$_2$), 2.39 (t, 2H, —CH$_2$), 1.90-2.04 (m, 4H, —CH$_2$), 1.05-1.70 (12H, —CH$_2$), 2.19, 0.89 (s, 6H, —CH$_3$).

Embodiment 6

A method for preparing a carbon source for wastewater treatment by using kitchen waste was different from Embodiment 5 in that the complex microbial inoculant was prepared by the present embodiment.

The complex microbial inoculant was different from Embodiment 5 in that the excipient was prepared by the present embodiment.

The preparation of the complex microbial inoculant was the same as Embodiment 5.

The excipient was an Fe-based MOF nanocomposite, and its preparation method was different from Embodiment 5 in that thioacetamide was used to replace N-(n-butyl) thiophosphoric triamide.

The preparation of a novel ionic liquid was the same as Embodiment 5.

Embodiment 7

A method for preparing a carbon source for wastewater treatment by using kitchen waste was different from Embodiment 1 in that the complex microbial inoculant was prepared by the present embodiment.

The complex microbial inoculant was different from Embodiment 1 in that the excipient was prepared by the present embodiment.

The preparation of the complex microbial inoculant was the same as Embodiment 1.

The excipient was an Fe-based MOF nanocomposite, and its preparation method was different from Embodiment 1 in that thioacetamide was used to replace N-(n-butyl) thiophosphoric triamide.

Embodiment 8

A method for preparing a carbon source for wastewater treatment by using kitchen waste was different from Embodiment 1 in that the complex microbial inoculant was prepared by the present embodiment.

The complex microbial inoculant was different from Embodiment 1 in that the excipient was a wood chip.

The preparation of the complex microbial inoculant was the same as Embodiment 1.

Embodiment 9

Application of a carbon source for wastewater treatment: feasibility research in SBR as a supplementary carbon source for a sewage plant A main part of an SBR reactor for a test was made of organic glass, with an effective volume of 2 L, and start and stop of an air compressor and an agitator and time for water inlet and outlet were controlled by manual timing, so that the operation of the device completely simulated an actual operation state of a sewage treatment plant. The SBR reactor ran for 2 cycles every day, and after precipitation, 0.5 L of water was discharged from a water outlet and 0.5 L of sewage entered from the water outlet (a drainage ratio of 1/4); a DO concentration of the SBR reactor in an aeration stage was controlled at 2-6 mg/L; and the dissolved oxygen in a stirring stage was controlled at 0.2-0.5 mg/L. Activated sludge was taken back from the sewage treatment plant, and connected to the SBR reactor after air exposure for 1 d; in the operation cycles, water entered and the activated sludge was stirred for 1.5 h to react (aerate) for 3 h, precipitate for 1 h, decant water for 1.5 h and idle for 0.5 h; and raw sewage was connected and the SBR reactor run for two days, so that an effluent of the reactor was stable. An addition amount of the carbon source sample accounted for 1.2% of the sewage. The SBR reactor ran for 2 d.

The main analysis and preparation of the test included COD, DO, $NH_4^+$—N, $NO_3^-$—N, TN, TP, etc., the water quality analysis was carried out in accordance with the method specified in Water and Wastewater Detection Analysis Method (4th Edition) compiled by the State Environmental Protection Administration, and the testing method was shown in Table 2:

TABLE 2

Testing method for water quality indexes

| Testing indexes | Units | Methods |
|---|---|---|
| COD | mg/L | Fast digestion method |
| NH4+-N | mg/L | Phenol-sodium hypochlorite colorimetric method |
| NO3--N | mg/L | Ultraviolet spectroscopy |
| TN | mg/L | HACH total nitrogen reagent |
| TP | mg/L | Ammonium molybdate spectrophotometric method |
| DO | mg/L | Rex DO-958 |
| Salinity | % | Salinometer HORIBA |
| SV30 | % | Volumetric method |
| MLSS | mg/L | Weight method |
| SVI | — | Weight method |

Sewage indexes were shown in Table 3:

TABLE 3

Physicochemical properties of sewage

| Indexes | TN (mg/L) | NH4+-N (mg/L) | TP (mg/L) | COD (mg/L) | pH |
|---|---|---|---|---|---|
| Concentration | 10.78 | 9.54 | 8.19 | 434.60 | 6.98 |

The effluent quality after adding the testing sample for SBR operation was shown in Table 4:

TABLE 4

Physicochemical properties of effluent quality

| Indexes | TN (mg/L) | NH4+-N (mg/L) | TP (mg/L) | COD (mg/L) | pH |
|---|---|---|---|---|---|
| Embodiment 1 | 2.51 | 0.58 | 0.21 | 23.56 | 6.98 |
| Embodiment 5 | 1.93 | 0.29 | 0.19 | 19.23 | 6.81 |
| Embodiment 6 | 2.79 | 0.64 | 0.25 | 23.74 | 6.95 |
| Embodiment 7 | 3.27 | 0.91 | 0.28 | 26.97 | 7.01 |
| Embodiment 8 | 3.43 | 1.03 | 0.30 | 27.83 | 7.03 |
| Blank control group | 4.95 | 1.42 | 0.41 | 28.42 | 7.10 |

Note: the carbon source for wastewater treatment was not added in the blank control group.

From the data analysis in Table 4, it could be seen that when compared with the blank control group, the concentrations of TN, $NH_4^+$—N and TP in the effluent quality decreased significantly after the sewage was treated by adding the carbon source prepared in Embodiment 8, but the concentration of COD did not change significantly; and effects of Embodiment 7 were slightly better than those of Embodiment 8, indicating that the carbon source prepared in the embodiment was added for sewage treatment to promote the removal effect of TN, $NH_4^+$—N and TP. Effects of Embodiment 1 were better than those of Embodiment 7, indicating that N-(n-butyl) thiophosphoric triamide was used to modify an Fe-based MOF nanocomposite, which was added to a complex microbial inoculant as an excipient, and acted on the degradation of kitchen waste to prepare the carbon source for wastewater treatment, so as to have a significant enhancement effect on sewage treatment. Effects of Embodiment 5 were better than those of Embodiment 1, and effects of Embodiment 6 were better than those of Embodiment 7, indicating that the novel ionic liquid prepared by the present invention was compounded with water to perform immersion treatment on the kitchen waste in advance, which could further enhance the degradation process of the kitchen waste, and the prepared carbon source showed a better enhancement effect on sewage treatment.

Investigation of Effects on the Activated Sludge $SV_{30}$ is a volume percent of the sludge after a mixed liquor is settled for 30 min in the aeration stage, which characterizes the sedimentation; the less the $SV_{30}$ value, the better the sedimentation of the sludge. MLSS further characterizes microbial biomass changes in the activated sludge in the SBR reactor.

The SVI change indicates that the doping of a phase-change liquid can maintain agglomeration and sedimentation of the activated sludge at a normal level. Generally, a good activated sludge SVI is often 50-120; the SVI value is too low, indicating that the sludge activity is not enough, which may be caused by the lack of nutrients in water; and the SVI value is too high, indicating that sludge bulking may occur.

The relevant testing results were shown in Table 5:

TABLE 5

Physicochemical properties of the activated sludge

| Indexes | $SV_{30}$ (%) | MLSS (mg/L) | SVI (mg/L) |
|---|---|---|---|
| Embodiment 1 | 24.5 | 5369.8 | 64.9 |
| Embodiment 5 | 24.8 | 5574.1 | 69.3 |
| Embodiment 6 | 24.4 | 5372.5 | 64.4 |
| Embodiment 7 | 24.6 | 5164.7 | 59.6 |
| Embodiment 8 | 24.7 | 5043.6 | 58.7 |
| Blank control group | 25.2 | 4768.5 | 54.3 |

Note: the carbon source for wastewater treatment was not added in the blank control group.

From the data analysis in Table 5, it could be seen that when compared with the blank control group, physicochemical indexes (MLSS and SVI values) of the activated sludge showed a significant increase after the sewage was treated by adding the carbon source prepared in Embodiment 8, but $SV_{30}$ did not change significantly; and effects of Embodiment 7 were slightly better than those of Embodiment 8, indicating that the carbon source prepared in the embodiment was added for sewage treatment to effectively promote the growth of microorganisms in the activated sludge and enhance the activity of the sludge, so that the activated sludge maintained excellent agglomeration and sedimentation. Effects of Embodiment 1 were better than those of Embodiment 7, indicating that N-(n-butyl) thiophosphoric triamide was used to modify an Fe-based MOF nanocomposite, which was added to a complex microbial inoculant as an excipient, and acted on the degradation of kitchen waste to prepare the carbon source for wastewater treatment, so as to have a significant enhancement effect on physicochemical properties of the activated sludge. Effects of Embodiment 5 were better than those of Embodiment 1, and effects of Embodiment 6 were better than those of Embodiment 7, indicating that the novel ionic liquid prepared by the present invention was compounded with water to perform immersion treatment on the kitchen waste in advance, which could further enhance the growth of microorganisms in the activated sludge and enhance the activity of the activated sludge, so that the carbon source had a more excellent sewage treatment capacity.

Test Example 1

X-Ray Photoelectron Spectroscopy Characterization

A radiation source for the test was a photon beam, and there was very little interference between different elements during the test. A model of an instrument for the test was ESCALAB 250.

The above test was performed on the Fe-based MOF nanocomposite prepared in Embodiment 1, and the result was shown in FIG. 1. From the analysis of FIG. 1, it could be seen that characteristic peaks of Fe, N, C, O, S and P appeared in an XPS picture of the Fe-based MOF nanocomposite prepared in Embodiment 1, which indicated the Fe-based MOF nanocomposite successfully prepared in Embodiment 1.

Test Example 2

Determination of Organic Matter 0.5 g of the sample was added to 25 mL of potassium dichromate solution-sulfuric acid solution, shaken well, then placed in a boiling water bath to perform heat preservation for 30 min, and shaken once every 5 min; then the mixture was taken out and cooled to room temperature, water was added to 120 mL, 6 drops of a phenanthroline indicator were added, and titrated to brownish red with a ferrous sulfate standard solution. Meanwhile, silicon dioxide was used to replace the sample to perform a blank experiment. Organic matter and the degradation rate of organic matter were calculated according to the following equations:

Organic matter (%)=$[c(V_0-V)\times0.003\times1.724]/[m(1-X_0)D]\times100$ wherein, c represents a molar concentration of the ferrous sulfate standard solution, mol/L; $V_0$ represents a volume of the ferrous sulfate standard titration solution when the blank experiment is performed, mL; V represents a volume of the ferrous sulfate standard solution used during determination, mL; 0.003 is the molar mass of a quarter carbon atom, g/mol; 1.724 is a coefficient of converting organic carbon to organic matter; m represents the mass of the sample, g; $X_0$ represents a water content of the air-dried sample; and D represents a dilution ratio: 50/250.

Degradation rate of organic matter (%)=(content of organic matter before degradation-content of organic matter after degradation)/content of organic matter before degradation×100

The above test was performed on the fermented material prepared after treatment in Embodiments 1-8, and the results were shown in Table 6:

TABLE 6

Testing results on degradation of organic matter

| Samples | Degradation rate of organic matter (%) |
|---|---|
| Embodiment 1 | 72.4 |
| Embodiment 2 | 73.1 |
| Embodiment 3 | 72.3 |
| Embodiment 4 | 72.5 |
| Embodiment 5 | 78.6 |
| Embodiment 6 | 73.4 |
| Embodiment 7 | 67.9 |
| Embodiment 8 | 64.8 |

From the data analysis in Table 6, it could be seen that the degradation rate of organic matter of the fermented material obtained after treatment in Embodiment 1 was higher than that of Embodiment 7 and Embodiment 8, and the effect of Embodiment 7 was slightly better than that of Embodiment 8, indicating that N-(n-butyl) thiophosphoric triamide was used to modify an Fe-based MOF nanocomposite, which was added to a complex microbial inoculant as an excipient, so as to effectively enhance the degradation of the inoculant on the kitchen waste. The effect of Embodiment 5 was better than that of Embodiment 1, and the effect of Embodiment 6 was better than that of Embodiment 7, indicating that the novel ionic liquid prepared by the present invention was compounded with water to perform immersion treatment on the kitchen waste in advance, which could further enhance the degradation process of the kitchen waste and improve the degradation effect of organic matter in the kitchen waste.

Test Example 3

A test on physicochemical indexes was performed on the carbon sources prepared in Embodiments 1-8, and the results were shown in Table 7:

TABLE 7

Main physicochemical properties of the carbon sources

| Indexes | TN (mg/L) | NH4+-N (mg/L) | TP (mg/L) | COD (mg/L) | C/N | pH |
|---|---|---|---|---|---|---|
| Embodiment 1 | 324.21 | 243.43 | 42.34 | 28214 | 43.5 | 6.73 |
| Embodiment 2 | 326.47 | 245.16 | 43.71 | 28364 | 44.1 | 6.62 |
| Embodiment 3 | 323.16 | 244.65 | 42.94 | 28296 | 43.8 | 6.80 |
| Embodiment 4 | 325.35 | 243.22 | 42.19 | 28210 | 43.3 | 6.71 |
| Embodiment 5 | 331.08 | 248.08 | 45.23 | 30467 | 48.4 | 6.77 |
| Embodiment 6 | 311.43 | 238.89 | 41.98 | 29006 | 45.9 | 6.82 |
| Embodiment 7 | 309.43 | 236.67 | 39.02 | 27105 | 41.7 | 6.85 |
| Embodiment 8 | 301.40 | 230.13 | 36.96 | 25810 | 40.6 | 6.67 |

From the data analysis in Table 7, it could be seen that the C/N ratio of the carbon source for wastewater treatment prepared in Embodiment 1 was higher than that of Embodiment 7 and Embodiment 8, and the effects of Embodiment 7 were slightly better than those of Embodiment 8, indicating that N-(n-butyl) thiophosphoric triamide was used to modify an Fe-based MOF nanocomposite, which was added to a complex microbial inoculant as an excipient, so as to effectively enhance the degradation process of the inoculant on the kitchen waste, increase the degradation rate and improve the contents of physicochemical properties of the prepared carbon sources. The effects of Embodiment 5 were better than those of Embodiment 1, and the effects of Embodiment 6 were better than those of Embodiment 7, indicating that the novel ionic liquid prepared by the present invention was compounded with water to perform immersion treatment on the kitchen waste in advance, which could further enhance the degradation process of the kitchen waste and adjust the contents of physicochemical properties of the prepared carbon sources.

The conventional art in the above embodiments is the prior art known to those skilled in the art, which will not be detailed herein.

The above are only specific embodiments of the present invention, but the protection scope of the present invention is not limited thereto; any person skilled in the art who is familiar with the art can easily think of changes or replacements within the technical scope disclosed in the present invention, which shall be covered within the protection scope of the present invention. Therefore, the protection scope of the present invention shall be subject to the protection scope of the claims.

What is claimed is:

1. A method for preparing a carbon source for wastewater treatment by using kitchen waste, comprising:
    adding a complex microbial inoculant into the kitchen waste; and
    phase-change degrading the kitchen waste into a phase-change liquid under aerobic fermentation of the complex microbial inoculant; wherein the phase-change liquid is the carbon source for wastewater treatment;
    the complex microbial inoculant comprises: a microbial agent comprising aerobic bacteria; and an excipient comprising an Fe-based metal-organic framework (MOF) nanocomposite;
    the Fe-based MOF nanocomposite is prepared by the following steps:
    mixing an Fe-based metal-organic framework and graphene oxide, performing one-step solvothermal synthesis to obtain Fe-MOF@GO, and then mixing the Fe-MOF @GO with N-(n-butyl) thiophosphoric triamide and performing high-temperature treatment to obtain the Fe-based MOF nanocomposite.

2. The method according to claim 1, wherein a mass ratio of the microbial agent to the excipient is 1:(3-10).

3. The method according to claim 1, wherein the microbial agent comprises 10-16 parts of *Bacillus licheniformis*, 15-20 parts of *Bacillus subtilis*, 8-14 parts of yeast and 10-15 parts of *Pediococcus acidilactici* in parts by weight.

4. The method according to claim 1, wherein the method specifically comprises the following steps:
    sorting and removing sundries from the kitchen waste, adding water according to a solid-liquid ratio of 1 g: (1-1.2) mL to obtain a mixture, placing the mixture in a pulverizer for crushing and pulping, filtering with a filter screen, heating the filtered kitchen waste slurry for 30-60 min at 75-90° C., and extracting and removing 70%-80% of waste grease with a three-phase separator;
    adding the complex microbial inoculant into the kitchen waste slurry, adjusting an initial pH value to 6.5-7.2, performing open fermentation at 35-45° C. for 4-6 d; and
    centrifuging the fermented material for 10-15 min at 4000-4200 rpm for solid-liquid separation, and taking a supernatant; wherein the supernatant is the carbon source for wastewater treatment.

5. The method according to claim 1, wherein a carbon-nitrogen ratio of the carbon source for wastewater treatment is greater than 40:1.

6. The method according to claim 1, wherein in the carbon source for wastewater treatment, a chemical oxygen demand (COD) content is 20000-40000 mg/L, a $NH_4^+$—N content is 200-600 mg/L, a total nitrogen (TN) content is 300-500 mg/L, and a total phosphorus (TP) content is 30-50 mg/L.

7. An application of the Fe-based MOF nanocomposite prepared by the method according to claim 1 in preparing the complex microbial inoculant for degradation of the kitchen waste.

8. An application of the Fe-based MOF nanocomposite prepared by the method according to claim 1 in preparing the carbon source for wastewater treatment.

\* \* \* \* \*